United States Patent [19]
Tripp et al.

[11] Patent Number: 5,792,624
[45] Date of Patent: Aug. 11, 1998

[54] DIROFILARIA AND ONCHOCERCA LARVAL L3 CYSTEINE PROTEASE PROTEINS AND USES THEREOF

[75] Inventors: Cynthia Ann Tripp; Nancy Wisnewski; Robert B. Grieve, all of Fort Collins; Glenn R. Frank, Wellington; Jennifer K. Richer, Denver, all of Colo.

[73] Assignees: Heska Corporation; Colorado State University Research Foundation, both of Fort Collins, Colo.

[21] Appl. No.: 482,282

[22] Filed: Jun. 7, 1995

Related U.S. Application Data

[63] Continuation-in-part of Ser. No. 153,554, Nov. 16, 1993, abandoned, and Ser. No. 101,283, Aug. 3, 1993, abandoned, which is a continuation of Ser. No. 654,226, Feb. 12, 1991, abandoned, said Ser. No. 153,554, is a continuation of Ser. No. 792,209, Nov. 12, 1991, abandoned.

[51] Int. Cl.[6] .................. C12P 21/06; C12P 21/04; A61K 38/00; C12N 15/00
[52] U.S. Cl. .................. 435/69.1; 435/71.1; 435/252.3; 435/320.1; 530/324; 935/22; 935/66
[58] Field of Search ............... 435/6, 69.1, 219, 435/226, 71.1, 252.3, 320.1; 530/324, 350; 536/235

[56] References Cited

PUBLICATIONS

Boulay et al., 1995, *Comp. Biochem. Physiol.,* 111B(3):353–359.
Boulay et al., 1996, *J. Comp. Physiol B,* 166:310–318.
Chung et al., 1995, *J. Parasitol.,* pp. 137–142.
Wijffels, 1994, *Biochem. J.,* 299:781–790 (Abstract).
Yamakami, 1995, *Eur. J. Biochem.,* 233:490–497.
Molecular SIGMA Biology catalog, A New Dimension, 1989, Oligonucleotide Products, p. 54.
Abraham et al., "In Vitro Culture of *Dirofilaria immitis* Third–and Fourth–Stage larvae under Defined Conditions," The Journal of Parasitology, vol. 73, No. 2, pp. 377–383, Apr. 1987.
Richer et al., "*Dirofilaria immitis*: Proteases Produced by Third–and Fourth–Stage Larvae," Experimental Parasitology, vol. 75, pp. 213–222, 1992.
J. Sambrook e tal., Molecular Cloning A Laboratory Manual, Second Edition, Cold Spring Harbor Laboratory Press, pp. 9.47–9.51, 1989.

*Primary Examiner*—Bradley L. Sisson
*Attorney, Agent, or Firm*—Heska Corporation; Colorado State University Research Foundation

[57] ABSTRACT

The present invention provides for filariid nematode cysteine protease proteins; to filariid nematode cysteine protease nucleic acid molecules, in particular, *Dirofilaria immitis* L3 larval cysteine protease nucleic acid molecules and *Onchocerca volvulus* L3 larval cysteine protease nucleic acid molecules; to antibodies raised against such proteins, and to compounds that inhibit filariid nematode cysteine protease activity. The present invention also includes methods to obtain such proteins, nucleic acid molecules, antibodies and/or inhibitors. The present invention also includes therapeutic compositions comprising such proteins, nucleic acid molecules, antibodies and/or inhibitors, and the use of such compositions to protect an animal from disease caused by parasitic helminths.

5 Claims, No Drawings

DIROFILARIA AND ONCHOCERCA LARVAL L3 CYSTEINE PROTEASE PROTEINS AND USES THEREOF

CROSS-REFERENCE TO RELATED APPLICATIONS

The present application is a continuation-in-part of U.S. patent application Ser. No. 08/153,554, filed Nov. 16, 1993, now abandoned entitled "PROTEASE VACCINE AGAINST HEARTWORM", which is a continuation U.S. patent application Ser. No. 07/792,209, filed Nov. 12, 1991 now abandoned. The present application is also a continuation-in-part of U.S. patent application Ser. No. 08/101,283, filed Aug. 3, 1993, now abandoned entitled, "REAGENTS AND METHODS FOR IDENTIFICATION OF VACCINES", which is a continuation of U.S. patent application Ser. No. 07/654,226, filed Feb. 12, 1991 now abandoned. Both applications are each incorporated by reference herein in its entirety.

FIELD OF THE INVENTION

The present invention relates to novel filarild nematode protease genes, proteins encoded by such genes, antibodies raised against such proteins, and protease inhibitors produced using such proteins. Particular proteases of the present invention include cysteine proteases. The present invention also includes therapeutic compositions comprising such nucleic acid molecules, proteins, antibodies and inhibitors, as well as their use to protect animals from disease caused by helminth parasites, such as by tissue-migrating helminths, including Dirofilaria and Onchocerca.

BACKGROUND OF THE INVENTION

Parasite infections in animals, including humans, are typically treated by chemical drugs, because there are essentially no efficacious vaccines available. One disadvantage with chemical drugs is that they must be administered often. For example, dogs susceptible to heartworm are typically treated monthly to maintain protective drug levels. Repeated administration of drugs to treat parasite infections, however, often leads to the development of resistant strains that no longer respond to treatment. Furthermore, many of the chemical drugs are harmful to the animals being treated, and as larger doses become required due to the build up of resistance, the side effects become even greater.

It is particularly difficult to develop vaccines against parasite infections both because of the complexity of the parasite's life cycle and because, while administration of parasites or parasite antigens can lead to the production of a significant antibody response, the immune response is typically not sufficient to protect the animal against infection.

As for most parasites, the life cycle of *Dirofilaria immitis*, the helminth that causes heartworm, includes a variety of life forms, each of which presents different targets, and challenges, for immunization. Adult forms of the parasite are quite large and preferentially inhabit the heart and pulmonary arteries of an animal. Sexually mature adults, after mating, produce microfilariae which traverse capillary beds and circulate in the vascular system. The microfilariae are ingested by female mosquitos during blood feeding on an infected dog, subsequent development of the microfilariae into two larval stages (L1 and L2) occurs in the mosquito. The microfilariae go through and finally become mature third stage larvae (L3) which can then be transmitted back to a dog through the bite of the mosquito. It is this L3 stage, therefore, that accounts for the initial infection. As early as three days after infection, the L3 molt to the fourth larval (L4) stage, and subsequently to the fifth stage, or immature adults. The immature adults migrate to the heart and pulmonary arteries, where they mature and reproduce, thus producing the microfilariae in the blood. "Occult" infection with heartworm in dogs is defined as an infection in which no microfilariae can be detected, but the existence of adult heartworms can be determined through thoracic examination.

Both the molting process and tissue migration are likely to involve the action of one or more enzymes, including proteases. Although protease activity has been identified in a number of parasites (including in larval excretory-secretory products) as well as in mammals, there has been no identification of a cysteine protease gene in any filariid nematode.

Cysteine protease genes have been isolated from several mammalian sources and from the nematodes *Haemonchus contortus* (e.g., Pratt et al., 1992, *Mol. Biochem. Parasitol.* 51, 209–218) and *Caenorhabditis elegans* (Ray et al., 1992, *Mol. Biochem. Parasitol.* 51, 239–250). In addition, consensus sequences, particularly around the active sites, have also been identified for serine and cysteine proteases; see, for example, Sakanari et al., 1989, *Proc. Natl. Acad. Sci. USA* 86, 4863–4867. The determination of these sequences, however, does not necessarily predict that the cloning of novel cysteine protease genes will be straight-forward, particularly since the sequences shared by different cysteine proteases are such that probes and primers based on the consensus sequences are highly degenerative.

Heartworm not only is a major problem in dogs, which typically are unable to develop immunity after infection (i.e., dogs can become reinfected even after being cured by chemotherapy), but is also becoming increasingly widespread in other companion animals, such as cats and ferrets. Heartworm infections have also been reported in humans. Other parasite infections are also widespread, and all require better treatment, including preventative vaccine programs and/or targeted drug therapies.

SUMMARY OF THE INVENTION

One embodiment of the present invention is an isolated filariid nematode nucleic acid molecule that hybridizes, under stringent hybridization conditions, with a *Dirofilaria immitis* L3 larval cysteine protease gene and/or an *Onchocerca volvulus* L3 larval cysteine protease gene. A preferred nucleic acid molecule of the present invention includes at least a portion of SEQ ID NO:1, SEQ ID NO:3, SEQ ID NO:5, SEQ ID NO:7, or an allelic variant of any of those nucleic acid sequences. The present invention also includes recombinant molecules and recombinant cells that include filariid nematode cysteine protease nucleic acid molecules of the present invention. Also included are methods to produce such nucleic acid molecules, recombinant molecules and recombinant cells of the present invention.

Another embodiment of the present invention is an isolated protein that includes a filariid nematode cysteine protease protein or a mimetope of such a protein. A filariid nematode cysteine protease protein of the present invention preferably has cysteine protease activity and/or comprises a protein that, when administered to an animal, is capable of eliciting an immune response against a natural helminth cysteine protease protein. The present invention also includes inhibitors of cysteine protease activity as well as antibodies that recognize (i.e., selectively bind to) a filariid nematode cysteine protease protein and/or mimetope thereof of the present invention. Also included are methods to produce such proteins, inhibitors and antibodies of the present invention.

Yet another embodiment of the present invention is a therapeutic composition capable of protecting an animal from disease caused by a parasitic helminth. Such a therapeutic composition comprises at least one of the following protective compounds: an isolated parasitic filariid nematode nucleic acid molecule that hybridizes under stringent hybridization conditions with a *Dirofilaria immitis* L3 larval cysteine protease gene and/or an *Onchocerca volvulus* L3 larval cysteine protease gene; an isolated filariid nematode L3 larval cysteine protease protein or a mimetope thereof; an isolated antibody that selectively binds to a filariid nematode L3 larval cysteine protease protein; and an inhibitor of cysteine protease activity identified by its ability to inhibit filariid nematode L3 larval cysteine protease activity. Also included is a method to protect an animal from disease caused by a parasitic helminth that includes administering to the animal a therapeutic composition of the present invention. A preferred therapeutic composition of the present invention is a composition capable of protecting an animal from heartworm.

The present invention also includes a method to identify a compound capable of inhibiting cysteine protease activity of a parasitic helminth. Such a method includes
(a) contacting an isolated filariid nematode L3 larval cysteine protease protein with a putative inhibitory compound under conditions in which, in the absence of the compound, the protein has cysteine protease activity; and
(b) determining if the putative inhibitory compound inhibits the activity. Also included is a test kit to identify a compound capable of inhibiting cysteine protease activity that includes an isolated filariid nematode L3 larval cysteine protease protein having cysteine protease activity and a means for determining the extent of inhibition of cysteine protease activity in the presence of a putative inhibitory compound.

DETAILED DESCRIPTION OF THE INVENTION

The present invention provides for filariid nematode L3 larval cysteine protease proteins and nucleic acid molecules, as well as, antibodies directed against filariid nematode L3 larval cysteine protease proteins. Also included in the present invention is the use of these proteins, nucleic acid molecules and antibodies as therapeutic compositions to treat parasitic helminth diseases as well as in other applications, such as those disclosed below.

One embodiment of the present invention is an isolated filariid nematode L3 larval cysteine protease protein. A cysteine protease is referred to herein as "CP." A CP that can be found in third stage larvae (L3) is referred to herein as L3 larval CP. That such a protease is referred to as an L3 larval protease does not preclude that protease from also being present in other life stages of a helminth. Indeed, *D. immitis* L3 CP is also found in fourth stage larvae (L4), suggesting that L3 CP's of the present invention, in general, can also be found in L4. Furthermore, the inventors discovered that immune dog serum prepared as disclosed in U.S. patent application Ser. No. 08/101,283 (ibid.), now abandoned, which has also published as PCT Publication Number WO 92/13560, by Grieve et al, published Aug. 20, 1992, and is incorporated by reference herein in its entirety selectively binds to larval CP's of the present invention, a finding that enabled isolation of the first filariid nematode CP nucleic acid molecule.

According to the present invention, an isolated, or biologically pure, protein, is a protein that has been removed from its natural milieu. As such, "isolated" and "biologically pure" do not necessarily reflect the extent to which the protein has been purified. An isolated CP protein of the present invention can be obtained from its natural source, can be produced using recombinant DNA technology or can be produced by chemical synthesis. As used herein, an isolated CP protein of the present invention can be a full-length protein or any homologue of such a protein. Examples of CP homologues include CP proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homologue includes at least one epitope capable of eliciting an immune response against a CP protein of the present invention. That is, when the homologue is administered to an animal as an immunogen, using techniques known to those skilled in the art, the animal will produce a humoral and/or cellular immune response against at least one epitope of a CP protein of the present invention. The ability of a protein to effect an immune response, can be measured using techniques known to those skilled in the art.

Homologues of CP proteins of the present invention can be the result of natural allelic variation or natural mutation. CP protein homologues of the present invention can also be produced using techniques known in the art including, but not limited to, direct modifications to the protein or modifications to the gene encoding the protein using, for example, classic or recombinant DNA techniques to effect random or targeted mutagenesis. Isolated proteins of the present invention, including homologues, can be identified in a straight-forward manner by the proteins' ability to elicit an immune response against filariid nematode CP proteins.

CP proteins of the present invention, including homologues of the full-length protein, have the further characteristic of being encoded by nucleic acid molecules that hybridize under stringent hybridization conditions to at least one of the following genes: (a) a gene encoding a *Dirofilaria immitis* L3 cysteine protease protein (i.e., a *D. immitis* CP gene); and (b) a gene encoding an *Onchocerca volvulus* L3 cysteine protease protein (i.e., an *O. volvulus* CP gene). It is to be noted that the term "a" or "an" entity refers to one or more of that entity; for example, a gene refers to one or more genes or at least one gene. As such, the terms "a" (or "an"), "one or more" and "at least one" can be used interchangeably herein. It is also to be noted that the terms "comprising", "including", and "having" can be used interchangeably.

As used herein, stringent hybridization conditions refer to standard hybridization conditions under which nucleic acid molecules, including oligonucleotides, are used to identify molecules having similar nucleic acid sequences. Such standard conditions are disclosed, for example, in Sambrook et al., 1989, *Molecular Cloning: A Laboratory Manual*, Cold Spring Harbor Labs Press.

As used herein, a *D. immitis* CP gene includes all nucleic acid sequences related to a natural *D. immitis* CP gene such as regulatory regions that control production of the *D. immitis* CP protein encoded by that gene (such as, but not limited to, transcription, translation or post-translation control regions) as well as the coding region itself. In one embodiment, a *D. immitis* CP gene includes the nucleic acid sequence SEQ ID NO:1. Nucleic acid sequence SEQ ID NO:1 represents the deduced sequence of a cDNA (complementary DNA) nucleic acid molecule denoted herein as nDiCP$_{1298}$, the production of which is disclosed in the Examples. It should be noted that since nucleic acid sequencing technology is not entirely error-free, SEQ ID NO:1 (as well as other nucleic acid and protein sequences presented herein), at best, represents an apparent nucleic acid sequence of the nucleic acid molecule encoding a *D. immitis* CP protein of the present invention.

In another embodiment, a *D. immitis* CP gene can be an allelic variant that includes a similar but not identical sequence to SEQ ID NO:1. An allelic variant of a *D. immitis* CP gene including SEQ ID NO:1 is a gene that occurs at essentially the same locus (or loci) in the genome as the gene including SEQ ID NO:1, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given parasitic helminth since the genome is diploid and/or among a group of two or more filariid nematodes.

Similarly, an *O. volvulus* CP gene includes all nucleic acid sequences related to a natural *O. volvulus* CP gene such as regulatory regions that control production of the *O. volvulus* CP protein encoded by that gene as well as the coding region itself. In one embodiment, an *O. volvulus* CP gene includes the nucleic acid sequence SEQ ID NO:5. Nucleic acid sequence SEQ ID NO:5 represents the deduced sequence of a cDNA (complementary DNA) nucleic acid molecule denoted herein as nOvCP$_{291}$, the production of which is disclosed in the Examples. In another embodiment, an *O. volvulus* CP gene can be an allelic variant that includes a similar but not identical sequence to SEQ ID NO:5.

The minimal size of a CP protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich.

As such, the minimal size of a nucleic acid molecule used to encode a CP protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of a CP protein homologue of the present invention is from about 4 to about 6 amino acids in length, with preferred sizes depending on whether a full-length, fusion, multivalent, or functional portions of such proteins are desired.

Protein homologues of the present invention preferably are capable of eliciting an immune response against a filariid nematode CP protein; of selectively binding to immune serum using techniques as disclosed in WO 92/13560 application Ser. No. 08/101,283 (ibid.); and/or of having cysteine protease activity. The minimum size of a protein capable of eliciting an immune response is a minimum size sufficient to form an epitope, a size that typically is at least from about 5 to about 9 amino acids. As is appreciated by those skilled in the art, an epitope can include amino acids that naturally are contiguous to each other as well as amino acids that, due to the tertiary structure of the natural protein, are in sufficiently close proximity to form an epitope. Methods to measure an immune response or cysteine protease activity are known to those of skill in the art.

Any filariid nematode CP protein is a suitable CP protein of the present invention. Suitable filariid nematodes from which to isolate CP proteins (including isolation of the natural protein or production of the protein by recombinant or synthetic techniques) include, but are not limited to, filariid nematodes of the genera Dirofilaria, Onchocerca, Acanthocheilonema, Brugia, Dipetalonema, Loa, Parafilaria, Setaria, Stephanofilaria and Wuchereria. Preferred filariid nematodes include nematodes of the genera Dirofilaria and Onchocerca, with *D. immitis*, the parasite that causes heartworm, and *O. volvulus*, the parasite that causes onchocerciasis, being more preferred.

A preferred filariid nematode CP protein of the present invention is a compound that when administered to an animal in an effective manner, is capable of protecting that animal from disease caused by a parasitic helminth. As such, the parasitic helminth is essentially incapable of causing disease in an animal that is immunized with a filariid nematode CP protein of the present invention. In accordance with the present invention, the ability of a CP protein of the present invention to protect an animal from disease by a parasitic helminth refers to the ability of that protein to treat, ameliorate and/or prevent disease, including infection leading to disease, caused by the parasitic helminth, preferably by eliciting an immune response against the parasitic helminth. Such an immune response can include humoral and/or cellular immune responses.

Suitable parasites to target include any parasite that is susceptible to inhibition of cysteine protease activity. In one embodiment, such a parasite is essentially incapable of causing disease in an animal administered a CP protein of the present invention. As such, a parasite to target includes any parasite that produces a protein having one or more epitopes that can be targeted by a humoral and/or cellular immune response against a CP protein of the present invention and/or that can be targeted by a compound that otherwise inhibits CP activity, thereby resulting in the reduced ability of the parasite to cause disease in an animal. Suitable and preferred parasites to target include those parasitic helminths disclosed above as being useful in the production of filariid nematode proteins of the present invention. Additional suitable and preferred parasitic helminths to target are listed elsewhere herein.

It is to be appreciated that the present invention also includes mimetopes of CP proteins of the present invention that can be used in accordance with methods as disclosed for CP proteins of the present invention. As used herein, a mimetope of a CP protein of the present invention refers to any compound that is able to mimic the activity of such a CP protein, often because the mimetope has a structure that mimics the CP protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of the present invention is a fusion protein that includes a filariid nematode CP protein-containing domain attached to a fusion segment. Inclusion of a fusion segment as part of a CP protein of the present invention can enhance the protein's stability during production, storage and/or use. Depending on the segment's characteristics, a fusion segment can also act as an immunopotentiator to enhance the immune response mounted by an animal immunized with a filariid nematode CP protein containing such a fusion segment. Furthermore, a fusion segment can function as a tool to simplify purification of a filariid nematode CP protein, such as to enable purification of the resultant fusion protein using affinity chromatography. A suitable fusion segment can be a domain of any size that has the desired function (e.g., imparts increased stability, imparts increased immunogenicity to a protein, and/or simplifies purification of a protein). It is within the scope of the present invention to use one or more fusion segments. Fusion segments can be joined to amino and/or carboxyl termini of the CP-containing domain of the protein. Linkages between fusion segments and CP-containing domains of fusion proteins can be susceptible to cleavage in order to enable straight-forward recovery of the CP-containing domains of such proteins. Fusion proteins are preferably produced by culturing a recombinant cell transformed with a fusion nucleic acid molecule that encodes a protein including the fusion segment attached to either the carboxyl and/or amino terminal end of a CP-containing domain.

Preferred fusion segments for use in the present invention include a glutathione binding domain, such as *Schistosoma japonicum* glutathione-S-transferase (GST) or a portion thereof capable of binding to glutathione; a metal binding domain, such as a poly-histidine segment capable of binding to a divalent metal ion; an immunoglobulin binding domain, such as Protein A, Protein G, T cell, B cell, Fc receptor or complement protein antibody-binding domains; a sugar binding domain such as a maltose binding domain from a maltose binding protein; and/or a "tag" domain (e.g., at least a portion of β-galactosidase, a strep tag peptide, other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide. An example of a particularly preferred fusion protein of the present invention is PHIS-PDiCP$_{314}$ production of which is disclosed herein.

Another embodiment of the present invention is a filariid nematode CP protein that also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from diseases caused, for example, by at least one infectious agent.

Examples of multivalent protective compounds include, but are not limited to, a CP protein of the present invention attached to one or more compounds protective against one or more other infectious agents, particularly an agent that infects humans, cats, dogs, cattle and/or horses, such as, but not limited to: viruses (e.g., caliciviruses, distemper viruses, hepatitis viruses, herpesviruses, immunodeficiency viruses, infectious peritonitis viruses, leukemia viruses, panleukopenia viruses, parvoviruses, rabies viruses, other cancer-causing or cancer-related viruses); bacteria (e.g., Leptospira, Rochalimaea); fungi and fungal-related microorganisms (e.g., Candida, Cryptococcus, Histoplasma); and other parasites (e.g., Babesia, Cryptosporidium, Eimeria, Encephalitozoon, Hepatozoon, Isospora, Microsporidia, Neospora, Nosema, Plasmodium, Pneumocystis, Toxoplasma, as well as helminth parasites, such as those disclosed herein). In one embodiment, a *D. immitis* CP protein of the present invention is attached to one or more additional compounds protective against heartworm. In another embodiment, an *O. volvulus* CP protein of the present invention is attached to one or more additional compounds protective against onchocerciasis.

A preferred filariid nematode CP protein of the present invention is a protein encoded by a nucleic acid molecule that hybridizes under stringent hybridization conditions with nucleic acid molecule nDiCP$_{1298}$ and/or nucleic acid molecule nOvCP$_{291}$. Such a CP protein is encoded by a nucleic acid molecule that hybridizes under stringent hybridization conditions with a nucleic acid molecule having nucleic acid sequence SEQ ID NO:1 and/or a nucleic acid molecule having nucleic acid sequence SEQ ID NO:5.

The nucleic acid molecule nDiCP$_{1298}$ contains an open reading frame which is represented herein by SEQ ID NO:1. The open reading frame in nDiCP$_{1298}$ (SEQ ID NO:1) extends from the first nucleotide up to the stop codon beginning at about nucleotide 1195 and encodes a protein of about 398 amino acids, denoted herein as PDiCP$_{398}$, the deduced amino acid sequence of which is represented herein as SEQ ID NO:2. The sequence represented by SEQ ID NO:1 suggests that an initiating methionine (ATG) may be located at about nucleotides 97 through 99. Assuming that this ATG represents the initiation (start) codon and that nucleotides 1195 through about nucleotide 1197 of SEQ ID NO:1 represent the termination (stop) codon, then SEQ ID NO:1 encodes a full-length *D. immitis* CP protein having an amino acid sequence of about 366 amino acids, denoted herein as PDiCP$_{366}$. That open reading frame is denoted herein as nucleic acid molecule nDiCP$_{1098}$ which spans from about nucleotide 97 through about nucleotide 1194 of SEQ ID NO:1.

Comparison of amino acid sequence SEQ ID NO:2 with amino acid sequences reported in GenBank indicates that the significant homology started at about amino acid 85 of SEQ ID NO:2, corresponding to an ATG codon in SEQ ID NO:1 spanning from about nucleotide 253 through about nucleotide 255. While not being bound by theory, this comparison suggests that the mature *D. immitis* cysteine protease is a protein of about 314 amino acids, denoted herein as PDiCP$_{314}$, which has the deduced amino acid sequence represented herein as SEQ ID NO:4. PDiCP$_{314}$ is encoded by a nucleic acid molecule of about 942 nucleotides, denoted herein as nDiCP$_{942}$, the nucleic acid sequence of which is represented herein as SEQ ID NO:3, which corresponds to a region spanning from about nucleotide 253 through about nucleotide 1194 of SEQ ID NO:1. Based on SEQ ID NO:4, PDiCP$_{314}$ has a calculated molecular weight of about 36.2 kD and an estimated pI of 9.36.

The nucleic acid molecule nOvCP$_{291}$ contains an open reading frame which is represented herein by SEQ ID NO:5. The open reading frame in nOvCP$_{291}$ (SEQ ID NO:5) extends from about the second nucleotide up to the stop codon beginning at about nucleotide 218 and encodes a protein of about 72 amino acids, denoted herein as POVCP$_{72}$, the deduced amino acid sequence of which is represented herein as SEQ ID NO:6. The coding region of POvCP$_{72}$ is encoded by the nucleic acid molecule nOvCP$_{216}$ which is represented herein as SEQ ID NO:7.

Preferred filariid nematode CP proteins of the present invention also include: proteins comprising amino acid sequences that are at least about 40%, preferably at least about 60%, more preferably at least about 75% and even more preferably at least about 90% identical to amino acid sequence SEQ ID NO:4; and proteins comprising an amino acid sequences that are at least about 70%, more preferably at least about 75%, even more preferably at least about 80% and even more preferably at least about 90% identical to amino acid sequence SEQ ID NO:6. More preferred filariid nematode CP proteins of the present invention include: proteins encoded by at least a portion of SEQ ID NO:1 and, as such, have amino acid sequences that include at least a portion of SEQ ID NO:2; and proteins encoded by at least a portion of SEQ ID NO:5 and, as such, have amino acid sequences that include at least a portion of SEQ ID NO:6.

Particularly preferred filariid nematode CP proteins of the present invention are proteins that include SEQ ID NO:2, SEQ ID NO:4, and/or SEQ ID NO:6 (including, but not limited to the encoded proteins, full-length proteins, processed proteins, fusion proteins and multivalent proteins) as well as proteins that are truncated homologues of proteins that include SEQ ID NO:2, SEQ ID NO:4, and/or SEQ ID NO:6. Even more preferred proteins include PDiCP$_{398}$, PDiCP$_{366}$, PDiCP$_{314}$, PHIS-PDiCP$_{314}$ and POvCP$_{72}$. Examples of methods to produce such proteins are disclosed herein, including in the Examples section.

Another embodiment of the present invention is an isolated filariid nematode nucleic acid molecule that hybridizes under stringent hybridization conditions with a gene selected from the group consisting of a *D. immitis* L3 larval cysteine protease gene and an *O. volvulus* L3 larval cysteine protease gene. The identifying characteristics of such genes are heretofore described. A nucleic acid molecule of the present invention can include an isolated natural filariid nematode CP gene or a homologue thereof, the latter of which is described in more detail below. A nucleic acid molecule of the present invention can include one or more regulatory regions, full-length or partial coding regions, or combinations thereof. The minimal size of a nucleic acid molecule of the present invention is the minimal size that can form a stable hybrid with one of the aforementioned genes under stringent hybridization conditions. Suitable and preferred filariid nematodes are disclosed above.

In accordance with the present invention, an isolated nucleic acid molecule is a nucleic acid molecule that is not in its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

An isolated filariid nematode CP nucleic acid molecule of the present invention can be obtained from its natural source either as an entire (i.e., complete) gene or a portion thereof capable of forming a stable hybrid with that gene. An isolated filariid nematode CP nucleic acid molecule can also be produced using recombinant DNA technology (e.g., polymerase chain reaction (PCR) amplification, cloning) or chemical synthesis. Isolated filariid nematode CP nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a filariid nematode CP protein of the present invention or to form stable hybrids under stringent conditions with natural gene isolates.

A filariid nematode CP nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., ability to elicit an immune response against at least one epitope of a filariid nematode CP protein) and/or by hybridization with a *D. immitis* CP gene and/or with an *O. volvulus* CP gene.

An isolated nucleic acid molecule of the present invention can include a nucleic acid sequence that encodes at least one filariid nematode CP protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a filariid nematode CP protein. As heretofore disclosed, filariid nematode CP proteins of the present invention include, but are not limited to, proteins having full-length filariid nematode CP coding regions, proteins having partial filariid nematode CP coding regions, fusion proteins, multivalent protective proteins and combinations thereof.

A preferred nucleic acid molecule of the present invention, when administered to an animal, is capable of protecting that animal from disease caused by a parasitic helminth. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein, the nucleic acid molecule being delivered to the animal by direct injection (i.e, as a naked nucleic acid) or in a vehicle such as a recombinant virus vaccine or a recombinant cell vaccine.

One embodiment of the present invention is a filariid nematode CP nucleic acid molecule that hybridizes under stringent hybridization conditions with the nucleic acid sequence nDiCP$_{1298}$ and/or the nucleic acid sequence nOvCP$_{291}$. The deduced nucleic acid sequence of nDiCP$_{1298}$ is represented herein as SEQ ID NO:1; and the deduced nucleic acid sequence of nOvCP$_{291}$, is represented herein as SEQ ID NO:5. An open reading frame contained in nDiCP$_{1298}$ is similar to that of known cysteine proteases and is referred to herein as nDiCP$_{942}$, is represented by SEQ ID NO:3. The open reading frame contained in nOvCP$_{291}$, referred to herein as nOvCP$_{216}$, is represented by SEQ ID NO:7.

A preferred nucleic acid molecule of the present invention includes at least a portion of nucleic acid sequence SEQ ID NO:1 or SEQ ID NO:5 that is capable of hybridizing to a *D. immitis* CP gene and/or to a *O. volvulus* CP gene of the present invention. More preferred is a nucleic acid molecule that includes nucleic acid sequence SEQ ID NO:1, SEQ ID NO:3, SEQ ID NO:5, and/or SEQ ID NO:7, or allelic variants thereof. Such a nucleic acid molecule can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound. Particularly preferred nucleic acid molecules include nDiCP$_{1298}$, nDiCP$_{1194}$, nDiCP$_{1098}$, nDiCP$_{942}$, nOvCP$_{291}$ and nOvCP$_{216}$.

The present invention also includes nucleic acid molecules encoding a protein having at least a portion of SEQ ID NO:2, nucleic acid molecules encoding a protein having at least a portion of SEQ ID NO:4, and nucleic acid molecules encoding a protein having at least a portion of SEQ ID NO:6, including nucleic acid molecules that have been modified to accommodate codon usage properties of the cells in which such nucleic acid molecules are to be expressed.

Knowing the nucleic acid sequences of certain filariid nematode CP nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain CP nucleic acid molecules for other filariid nematodes, particularly since, as described in detail in the Examples section, knowledge of *D. immitis* CP nucleic acid molecules of the present invention enabled the isolation of *O. volvulus* CP nucleic acid molecules of the present invention. Such nucleic acid molecules can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Preferred libraries to screen or from which to amplify nucleic acid molecule include parasitic helminth L3 larval libraries as well as genomic DNA libraries. Similarly, preferred DNA sources to screen or from which to amplify nucleic acid molecules include parasitic helminth L3 larval DNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising filariid nematode CP genes or other filariid nematode CP nucleic acid molecules. Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit CP protein production or activity. Such therapeutic applications include the use of such oligonucleotides in, for example, antisense-, triplex formation-, ribozyme- and/or RNA drug-based technologies. The present invention, therefore, includes such oligonucleotides and methods to protect animals from disease caused by parasitic helminths by use of one or more of such technologies. Appropriate oligonucleotide-containing therapeutic compositions can be administered to an animal, using techniques known to those skilled in the art, either prior to or after infection by a parasitic helminth such as *D. immitis* or *O. volvulus* in order to protect the animal from disease.

The present invention also includes a recombinant vector, which includes at least one filariid nematode CP nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule (s) are derived. The vector can be either RNA or DNA, either prokaryotic or eukaryotic, and typically is a virus or a plasmid. Recombinant vectors can be used in the cloning, sequencing, and/or otherwise manipulating of filariid nematode CP nucleic acid molecules of the present invention. One type of recombinant vector, referred to herein as a recombinant molecule and described in more detail below, can be used in the expression of nucleic acid molecules of the present invention. Preferred recombinant vectors are capable of replicating in the transformed cell.

Suitable and preferred nucleic acid molecules to include in recombinant vectors of the present invention are as disclosed herein for suitable and preferred filariid nematode CP nucleic acid molecules per se. Particularly preferred nucleic acid molecules to include in recombinant vectors, and particularly in recombinant molecules, of the present invention include nDiCP$_{1298}$, nDiCP$_{1194}$, nDiCP$_{1098}$, nDiCP$_{942}$, nOvCP$_{291}$ and nOvCP$_{216}$.

Isolated filariid nematode CP proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell that is capable of expressing the protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Suitable and preferred nucleic acid molecules with which to transform a cell are as disclosed herein for suitable and preferred filariid nematode CP nucleic acid molecules per se. Particularly preferred nucleic acid molecules to include in recombinant cells of the present invention include $nDiCP_{1298}$, $nDiCP_{1194}$ $nDiCP_{1098}$, $nDiCP_{942}$, $nOvCP_{291}$ and $nOvCP_{216}$.

Suitable host cells to transform include any cell that can be transformed with a nucleic acid molecule of the present invention. Host cells can be either untransformed cells or cells that are already transformed with at least one nucleic acid molecule. Host cells of the present invention either can be endogenously (i.e., naturally) capable of producing filariid nematode CP proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), insect, other animal and plant cells. Preferred host cells include bacterial, mycobacterial, yeast, helminth, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi; Salmonella typhimurium*, including attenuated strains such as UK-1 $_{\chi}3987$ and SR-11 $_{\chi}4072$; *Spodoptera frugiperda; Trichoplusia ni;* BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, $LMTK^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, helminth or other parasite, insect and mammalian cells and more preferably in the cell types heretofore disclosed.

Recombinant molecules of the present invention may also (a) contain secretory signals (i.e., signal segment nucleic acid sequences) to enable an expressed filariid nematode CP protein of the present invention to be secreted from the cell that produces the protein and/or (b) contain fusion sequences which lead to the expression of nucleic acid molecules of the present invention as fusion proteins. Examples of suitable signal segments and fusion segments encoded by fusion segment nucleic acids are disclosed herein. Eukaryotic recombinant molecules may include intervening and/or untranslated sequences surrounding and/or within the nucleic acid sequences of nucleic acid molecules of the present invention.

Suitable signal segments include natural signal segments or any heterologous signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments.

Nucleic acid molecules of the present invention can be operatively linked to expression vectors containing regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth or other parasite, insect and mammalian cells, such as, but not limited to, tac, lac, trp, trc, oxy-pro omp/lpp, rrnB, bacteriophage lambda ($\lambda$) (such as $\lambda P_L$ and $\lambda p_R$ and fusions that include such promoters), bacteriophage T7, T7lac, bacteriophage T3, bacteriophage SP6, bacteriophage SP01, metallothionein, $\alpha$-mating factor, Pichia alcohol oxidase, alphavirus subgenomic promoters (such as Sindbis virus subgenomic promoters), antibiotic resistance gene, baculovirus, *Heliothis zea* insect virus, vaccinia virus, herpesvirus, poxvirus, adenovirus, cytomegalovirus (such as intermediate early promoters, simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a filariid nematode nucleic acid molecule, such as a *D. immitis* or *O. volvulus* molecule prior to isolation.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein. Particularly preferred recombinant molecules include, pβgal-nDiCP$_{1298}$, pHis-nDiCP$_{945}$, and pVL1393-nCP$_{945}$. Details regarding the production of D. immitis CP nucleic acid molecule-containing recombinant molecules are disclosed herein. O. volvulus CP recombinant molecules are produced in a similar manner.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein. Particularly preferred recombinant cells include E. coli:pHis-nDiCP$_{945}$ and S. frugiperda:pVL1393-nDiCP$_{945}$. Details regarding the production of these recombinant cells are disclosed herein. O. volvulus CP recombinant cells are produced in a similar manner.

Recombinant cells of the present invention can also be co-transformed with one or more recombinant molecules including filariid nematode CP nucleic acid molecules encoding one or more proteins of the present invention and one or more other proteins useful in the production of multivalent vaccines which can include one or more protective compounds.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

In accordance with the present invention, recombinant cells of the present invention can be used to produce one or more proteins of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing a filariid nematode CP protein of the present invention. Such a medium is typically an aqueous medium comprising assimilable carbon, nitrogen and phosphate sources, as well as appropriate salts, minerals, metals and other nutrients, such as vitamins. The medium may comprise complex nutrients or may be a defined minimal medium. Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in E. coli; or be retained on the outer surface of a cell or viral membrane.

The phrase "recovering the protein" refers simply to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and should be capable of stimulating the production of antibodies in a treated animal.

The present invention also includes isolated antibodies capable of selectively binding to a filariid nematode CP protein of the present invention or to a mimetope thereof. Such antibodies are also referred to herein as anti-filariid nematode CP antibodies. Particularly preferred antibodies of this embodiment include anti-D. immitis CP antibodies and anti-O. volvulus CP antibodies.

Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees.

As used herein, the term "selectively binds to" refers to the ability of antibodies of the present invention to preferentially bind to specified proteins and mimetopes thereof of the present invention. Binding can be measured using a variety of methods known to those skilled in the art including immunoblot assays, immunoprecipitation assays, radioimmunoassays, enzyme immunoassays (e.g., ELISA), immunofluorescent antibody assays and immunoelectron microscopy; see, for example, Sambrook et al., ibid. An anti-filariid nematode CP antibody preferably binds to a filariid nematode CP protein in such a way as to reduce the activity of that protein.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Antibodies of the present invention also include chimeric antibodies that can bind to more than one epitope. Preferred antibodies are raised in response to proteins, or mimetopes thereof, that are encoded, at least in part, by a nucleic acid molecule of the present invention.

A preferred method to produce antibodies of the present invention includes (a) administering to an animal an effective amount of a protein or mimetope thereof of the present invention to produce the antibodies and (b) recovering the antibodies. In another method, antibodies of the present invention are produced recombinantly using techniques as heretofore disclosed to produce filariid nematode CP proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from parasitic helminths susceptible to treatment by such antibodies, (b) as reagents in assays to detect infection by such filariid nematodes and/or (c) as tools to screen expression libraries and/or to recover desired proteins of the present invention from a mixture of proteins and other contaminants. Furthermore, antibodies of the present invention can be used to target cytotoxic agents to parasitic helminths of the present invention in order to directly kill such helminths. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal in an effective manner, is capable of protecting that animal from disease caused by a parasitic helminth. Therapeutic compositions of the present invention include at least one of the following protective compounds: (a) an isolated filariid nematode L3 larval cysteine protease protein or a mimetope thereof; (b) an isolated filariid nematode nucleic acid molecule that hybridizes under stringent hybridization conditions with a *D. immitis* L3 larval cysteine protease gene and/or an *O. volvulus* L3 larval cysteine protease gene; (c) an isolated antibody that selectively binds to a filariid nematode L3 larval cysteine protease protein; (d) an inhibitor of cysteine protease activity identified by its ability to inhibit filariid nematode L3 larval cysteine protease activity; and (e) a mixture (i.e., combination) of at least two of the compounds. As used herein, a protective compound refers to a compound that, when administered to an animal in an effective manner, is able to treat, ameliorate, and/or prevent disease caused by a parasitic helminth of the present invention. Suitable helminths to target include a parasite comprises a tissue-migrating helminth. Preferred helminths to target include, for example, nematodes, cestodes and trematodes. More preferred helminths to target include, for example, filariid, ascarid, strongyle and trichostrongyle nematodes. Even more preferred helminths to target include, for example, nematodes of the genera Acanthocheilonema, Aelurostrongylus, Ancylostoma, Angiostrongylus, Ascaris, Brugia, Bunostomum, Dictyocaulus, Dioctophyme, Dipetalonema, Dirofilaria, Dracunculus, Filaroides, Lagochilascaris, Loa, Mansonella, Muellerius, Necator, Onchocerca, Parafilaria, Parascaris, Protostrongylus, Setaria, Stephanofilaria, Strongyloides, Strongylus, Thelazia, Toxascaris, Toxocara, Trichinella, Uncinaria and Wuchereria. Other particularly preferred parasitic helminths include nematodes of the genera Capillaria, Chabertia, Cooperia, Enterobius, Haemonchus, Nematodirus, Oesophagostomum, Ostertagia, Trichostrongylus and Trichuris. Particularly preferred nematodes include Dirofilaria, Onchocerca, Acanthocheilonema, Brugia, Dipetalonema, Loa, Parafilaria, Setaria, Stephanofilaria and Wuchereria filariid nematodes, with Dirofilaria and Onchocerca being more preferred. Examples of proteins, nucleic acid molecules and antibodies of the present invention are disclosed herein.

The present invention also includes a therapeutic composition comprising at least one filariid nematode CP-based compound of the present invention in combination with at least one additional compound protective against one or more infectious agents. Examples of such compounds and infectious agents are disclosed herein.

Therapeutic compositions of the present invention can be administered to any animal susceptible to such therapy, preferably to mammals, and more preferably to dogs, cats, humans, ferrets, horses, cattle, sheep and other pets, economic food animals and/or zoo animals. Preferred animals to protect against heartworm include dogs, cats, humans and ferrets, with dogs and cats being particularly preferred. Preferred animals to protect against onchocerciasis include humans, cattle and horses, with humans being particularly preferred.

In one embodiment, a therapeutic composition of the present invention can be administered to the vector in which the parasitic helminth develops, such as to a mosquito in order to prevent the spread of heartworm or to a black fly in order to prevent the spread of onchocerciasis. Such administration could be orally or by developing transgenic vectors capable of producing at least one therapeutic composition of the present invention. In another embodiment, a vector, such as a mosquito or a black fly, can ingest therapeutic compositions present in the blood of a host that has been administered a therapeutic composition of the present invention.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the therapeutic composition can also include an immunopotentiator, such as an adjuvant or a carrier. Adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax™ adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioredible).

A preferred controlled release formulation of the present invention is capable of releasing a composition of the present invention into the blood of the treated animal at a constant rate sufficient to attain therapeutic dose levels of the composition to protect an animal from disease caused by parasitic helminths. The therapeutic composition is preferably released over a period of time ranging from about 1 to about 12 months. A controlled release formulation of the present invention is capable of effecting a treatment for preferably at least about 1 month, more preferably at least about 3 months and even more preferably for at least about 6 months, even more preferably for at least about 9 months, and even more preferably for at least about 12 months.

In order to protect an animal from disease caused by a parasitic helminth of the present invention, a therapeutic composition of the present invention is administered to the animal in an effective manner such that the composition is capable of protecting that animal from a disease caused by a parasitic helminth. For example, an isolated protein or mimetope thereof, when administered to an animal in an effective manner, is able to elicit (i.e., stimulate) an immune response, preferably including both a humoral and cellular response, that is sufficient to protect the animal from the disease. Similarly, an antibody of the present invention, when administered to an animal in an effective manner, is administered in an amount so as to be present in the animal at a titer that is sufficient to protect the animal from the disease, at least temporarily. Oligonucleotide nucleic acid molecules of the present invention can also be administered in an effective manner, thereby reducing expression of filariid nematode CP proteins in order to interfere with development of parasitic helminths targeted in accordance with the present invention.

Therapeutic compositions of the present invention can be administered to animals prior to infection in order to prevent infection and/or can be administered to animals after infection in order to treat disease caused by the parasitic helminth. For example, proteins, mimetopes thereof, and antibodies thereof can be used as immunotherapeutic agents.

Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram (μg) to about 10 milligrams (mg) of the therapeutic composition per kilogram body weight of the animal. Booster vaccinations can be administered from about 2 weeks to several years after the original administration. Booster vaccinations preferably are administered when the immune response of the animal becomes insufficient to protect the animal from disease. A preferred administration schedule is one in which from about 10 μg to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal and intramuscular routes.

According to one embodiment, a nucleic acid molecule of the present invention can be administered to an animal in a fashion to enable expression of that nucleic acid molecule into a protective protein or protective RNA (e.g., antisense RNA, ribozyme or RNA drug) in the animal to be protected from disease. Nucleic acid molecules can be delivered to an animal in a variety of methods including, but not limited to, (a) administering a naked (i.e., not packaged in a viral coat or cellular membrane) nucleic acid vaccine (e.g., as naked DNA or RNA molecules, such as is taught, for example in Wolff et al., 1990, *Science* 247, 1465–1468) or (b) administering a nucleic acid molecule packaged as a recombinant virus vaccine or as a recombinant cell vaccine (i.e., the nucleic acid molecule is delivered by a viral or cellular vehicle).

A naked nucleic acid vaccine of the present invention includes a nucleic acid molecule of the present invention and preferably includes a recombinant molecule of the present invention that preferably is replication, or otherwise amplification, competent. Such a vaccine can comprise any nucleic acid molecule or recombinant molecule of the present invention. Preferred naked nucleic acid vaccines include at least a portion of a viral genome (i.e., a viral vector). Preferred viral vectors include those based on alphaviruses, poxviruses, adenoviruses, herpesviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), Rous Sarcoma Virus long terminal repeat, and tissue-specific transcription control sequences, as well as transcription control sequences endogenous to viral vectors if viral vectors are used. The incorporation of "strong" poly(A) sequences are also preferred.

Naked nucleic acid vaccines of the present invention can be administered in a variety of ways, with intramuscular, subcutaneous, intradermal, transdermal, intranasal and oral routes of administration being preferred. A preferred single dose of a naked nucleic acid vaccine ranges from about 1 nanogram (ng) to about 100 μg, depending on the route of administration and/or method of delivery, as can be determined by those skilled in the art. Suitable delivery methods include, for example, by injection, as drops, aerosolized and/or topically. Suitable excipients include, for example, physiologically acceptable aqueous solutions (e.g., phosphate buffered saline as well as others disclosed above), liposomes (including neutral or cationic liposomes), and other lipid membrane-based vehicles (e.g., micelles or cellular membranes).

A recombinant virus vaccine of the present invention includes a recombinant molecule of the present invention that is packaged in a viral coat and that can be expressed in an animal after administration. Preferably, the recombinant molecule is packaging-deficient. A number of recombinant viruses can be used, including, but not limited to, those based on alphaviruses, poxviruses, adenoviruses, herpesviruses, and retroviruses. Preferred recombinant virus vaccines are those based on alphaviruses (such as Sindbis virus), species-specific herpesviruses and species-specific poxviruses. Methods to produce and use recombinant virus vaccines are disclosed in PCT Publication No. WO 94/17813, by Xiong et al., published Aug. 18, 1994, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from disease caused by a parasitic helminths as disclosed herein. For example, a recombinant virus vaccine comprising a D. immitis CP nucleic acid molecule of the present invention is administered according to a protocol that results in the animal producing a sufficient immune response to protect itself from heartworm. A preferred single dose of a recombinant virus vaccine of the present invention is from about $1\times10^4$ to about $1\times10^7$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells of the present invention that express at least one protein of the present invention. Preferred recombinant cells for this embodiment include Salmonella, E. coli, Listeria, Mycobacterium, S. frugiperda, BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells or cell lysates.

The efficacy of a therapeutic composition of the present invention to protect an animal from disease caused by a parasitic helminth can be tested in a variety of ways including, but not limited to, detection of protective antibodies (using, for example, proteins or mimetopes of the present invention), detection of cellular immunity within the treated animal, or challenge of the treated animal with the parasitic helminth to determine whether the treated animal is resistant to disease. Such techniques are known to those skilled in the art.

One preferred embodiment of the present invention is the use of filariid nematode CP proteins, nucleic acid molecules and antibodies of the present invention, and particularly D. immitis CP proteins, nucleic acid molecules and antibodies of the present invention, to protect an animal from heartworm. Preferred therapeutic compositions are those that are able to inhibit at least one step in the portion of the parasite's development cycle that includes L3 larvae, third molt, L4 larvae, fourth molt and immature adult prior to entering the circulatory system. In dogs, this portion of the development cycle is about 70 days. Particularly preferred therapeutic compositions include D. immitis-based therapeutic compositions of the present invention. Such compositions are administered to animals in a manner effective to protect the animals from heartworm. Additional protection may be obtained by administering additional protective compounds, including other D. immitis proteins, nucleic acid molecules and antibodies.

Another preferred embodiment of the present invention is the use of filariid nematode CP proteins, nucleic acid molecules and antibodies of the present invention, and particularly O. volvulus CP proteins, nucleic acid molecules and antibodies of the present invention, to protect a human from onchocerciasis. Preferred therapeutic compositions are those that are able to inhibit at least one step in the portion of the parasite's development cycle that includes L3 larvae, third molt, L4 larvae, fourth molt and immature adult prior to entering the subcutaneous tissues. In humans infected with O. volvulus, this portion of the development cycle is about 150 days. Particularly preferred therapeutic compositions include O. volvulus-based therapeutic compositions of the present invention. Such compositions are administered to humans in a manner effective to protect the treated humans from onchocerciasis. Additional protection may be obtained by administering additional protective compounds, including other Onchocerca, preferably O. volvulus, proteins, nucleic acid molecules and antibodies.

An inhibitor of cysteine protease activity can be identified using parasitic helminth, and preferably D. immitis and/or O. volvulus CP proteins of the present invention. One embodiment of the present invention is a method to identify a compound capable of inhibiting cysteine protease activity of a parasitic helminth. Such a method includes the steps of (a) contacting (e.g., combining, mixing) an isolated filariid nematode CP protein with a putative inhibitory compound under conditions in which, in the absence of the compound, the protein has cysteine protease activity, and (b) determining if the putative inhibitory compound inhibits the cysteine protease activity. Putative inhibitory compounds to screen include organic molecules, antibodies (including mimetopes thereof) and substrate analogs. Methods to determine cysteine protease activity are known to those skilled in the art.

It is also within the scope of the present invention to use isolated proteins, mimetopes, nucleic acid molecules and antibodies of the present invention as diagnostic reagents to detect infection by parasitic helminths. Such diagnostic reagents can be supplemented with additional compounds that can detect other phases of the parasite's life cycle.

The following examples are provided for the purposes of illustration and are not intended to limit the scope of the present invention.

EXAMPLES

Example 1

This Example describes the cloning and sequencing of a filariid nematode cysteine protease nucleic acid molecule of the present invention.

A *D. immitis* cysteine protease nucleic acid molecule of about 1298 nucleotides, denoted nDiCP$_{1298}$1, was identified by its ability to encode a protein that selectively bound to at least one component of immune serum collected from a dog immunized with chemically abbreviated *D. immitis* larval infections in the following manner. A *D. immitis* cDNA expression library was constructed in Uni-ZAP™ XR vector (available from Stratagene Cloning Systems, La Jolla, Calif.), using Stratagene's ZAP-cDNA Synthesis Kit protocol and third stage larval mRNAs. Using the protocol described in the Stratagene picoBlue immunoscreening kit, the L3 larval cDNA expression library was screened with immune dog sera. The production and use of immune dog serum to identify heartworm vaccine candidates is disclosed in U.S. patent application Ser. No. 08/101,283, ibid, which is incorporated by reference herein in its entirety. Ser. No. 08/101,283 is a continuation of U.S. patent application Ser. No. 07/654,226, ibid, also published as PCT Publication No. WO 92/13560 on Aug. 20, 1992.

Immunoscreening of duplicate plaque lifts of the cDNA library with the same immune dog serum identified the nucleic acid molecule nDiCP$_{1298}$. The plaque-purified clone including nDiCP$_{1298}$ was converted into a double-stranded plasmid using ExAssist™ helper phage and SOLR™ *E. coli* according to the in vivo excision protocol described in the Stratagene ZAP-cDNA Synthesis Kit. Double-stranded plasmid DNA was prepared using an alkaline lysis protocol, such as that described in Sambrook et al., ibid. The double-stranded plasmid containing the fragment is denoted herein as recombinant molecule pβgal-nDiCP$_{1298}$. Pursuant to 37 CFR § 1.802 (a–c), SOLR™ *E. coli* comprising recombinant molecule pβgal-nDiCP$_{1298}$, designated herein as *E. coli*:pβgal-nDiCP$_{1298}$, was deposited with the American Type Culture Collection (ATCC, 12301 Parklawn Drive, Rockville, Md., 20852) under the Budapest Treaty as ATCC Accession No. ATCC 98471 on Jun. 18, 1997. Pursuant to 37 CFR§ 1.806, the deposit is made for a term of at least thirty (30) years and at least five (5) years after the most recent request for the furnishing of a sample of the deposit was received by the depository. Pursuant to 37 CFR § 1808 (a) (2), all restrictions imposed by the depositor on the availability to the public will be irrevocably removed upon the granting of the patent. The plasmid DNA was digested with EcoRI and XhoI restriction endonucleases. The digestion released two *D. immitis* DNA fragments of about 450 and about 848 nucleotides from the nDiCP$_{1298}$ nucleic acid molecule. As described in more detail below, nucleic acid molecule nDiCP$_{1298}$ has been shown to encode a cysteine protease protein.

Nucleic acid molecule nDiCP$_{1298}$ was sequenced using the Sanger dideoxy chain termination method, as described in Sambrook et al., ibid. An about 1298 nucleotide consensus sequence of the entire nDiCP$_{1298}$ nucleic acid molecule was determined and is presented as SEQ ID NO:1. The nucleic acid sequence SEQ ID NO:1 includes an open reading frame spanning from about nucleotide 1 through about nucleotide 1194, with a first ATG codon spanning from about nucleotide 97 through about nucleotide 99 and a termination (stop) codon spanning from about nucleotide 1195 through about 1197. A putative polyadenylation signal (5' AATAAA 3') is located from about nucleotide 1265 through about nucleotide 1270.

The open reading frame extending from the first nucleotide of nDiCP$_{1298}$ up to the stop codon is a nucleic acid molecule of about 1194 nucleotides, denoted herein as nDiCP$_{1194}$, which encodes a protein of about 398 amino acids, denoted herein as PDiCP$_{398}$, the deduced amino acid sequence of which is represented herein as SEQ ID NO:2. Assuming that the ATG located from about nucleotide 97 through about nucleotide 99 represents the initiation (start) codon, SEQ ID NO:1 encodes a protein having an amino acid sequence of about 366 amino acids, denoted herein as PDiCP$_{366}$. That open reading frame is denoted herein as nucleic acid molecule nDiCP$_{1098}$ and spans from about nucleotide 97 through about nucleotide 1194 of SEQ ID NO:1.

A homology search of the non-redundant protein sequence database was performed through the National Center for Biotechnology Information using the BLAST network. This database includes+SwissProt+PIR+SPUpdate+GenPept+GPUpdate. The search was performed using SEQ ID NO:2 and showed that SEQ ID NO:2 showed significant homology to certain cysteine proteases. That is, comparison of amino acid sequence SEQ ID NO:2 with amino acid sequences reported in GenBank indicates that the significant homology started at about amino acid 85 of SEQ ID NO:2, corresponding to an ATG codon in SEQ ID NO:1 spanning from about nucleotide 253 through about nucleotide 255. While not being bound by theory, this comparison suggests that the mature *D. immitis* cysteine protease is a protein of about 314 amino acids, denoted herein as PDiCP$_{314}$, which has the deduced amino acid sequence represented herein as SEQ ID NO:4. PDiCP$_{314}$ is encoded by a nucleic acid molecule of about 942 nucleotides, denoted herein as nDiCP$_{942}$, the nucleic acid sequence of which is represented herein as SEQ ID NO:3, which corresponds to a region spanning from about nucleotide 253 through about nucleotide 1194 of SEQ ID NO:1. Based on SEQ ID NO:4, PDiCP$_{314}$ has a calculated molecular weight of about 36.2 kD and an estimated pI of 9.36.

SEQ ID NO:4 was found to be about 37% identical to Norway lobster cathepsin L (Genbank Acc. No. S47433); about 30% identical to Dictyostelium discoideum cysteine proteinase 2 (Acc. No. X03344); about 39% identical to Sarcophaga peregrina pro-cathepsin (Acc. No. LD16533); about 36% identical to *Fasciola hepatica* cathepsin L-like proteinases (Acc. No. S43991); about 35% identical to *Fasciola hepatica* cathepsin (Acc. No. L33772); about 36% identical to *Schistosoma mansoni* cathepsin L (Acc. No. S44151); about 36% identical to *Fasciola hepatica* cathepsin L-like protease (Acc. No. Z22765); about 30% identical to *Trichomonas vaginalis* putative cysteine proteinase (Acc. No. X77221); about 35% identical to *Entamoeba histolytica* cysteine proteinase (Acc. No. A23705); and about 28% identical to *Trichomonas vaginalis* cysteine proteinase (Acc. No. S41427).

The corresponding region of SEQ ID NO:4 is also about 23% identical to the deduced amino acid sequence of the *D. immitis* amplified genomic PCR fragment nDiCP$_{143}$ disclosed in PCT Publication WO 95/32988 by Tripp, et al., published Dec. 7,1995, which claims priority from U.S. patent application Ser. No. 08/249,552, filed May 26, 1994, now abandoned. PCT Publication WO 95/32988 is incorporated by reference herein in its entirety.

Example 2

This example discloses the production of a recombinant cell of the present invention.

Recombinant molecule pHis-nDiCP$_{145}$, containing *D. immitis* cysteine protease nucleic acid molecule nDiCP$_{945}$ operatively linked to trc transcription control sequences and to a fusion sequence encoding a poly-histidine segment comprising 6 histidines, was produced in the following manner. An about 945 nucleotide DNA fragment containing nucleotides spanning from about nucleotide 253 through about nucleotide 1197 of SEQ ID NO:1, called nDiCP$_{945}$, was polymerase chain reaction (PCR) amplified from recombinant molecule pβgal-nDiCP$_{1298}$, described in Example 1, using the following primers: primers CP sen 5' AACGGTGAGGATCCAGCGAT-GAAAAAATTAGAAAC 3' (SEQ ID NO:8) (BamHI site in bold) and CP ant 5' ATTAAAAGATCTTTATATGGG-GAATGAAGCCATCG 3' (SEQ ID NO:9) (BglII site in bold). The PCR product was digested with BamHI and BglII restriction endonucleases, gel purified and subcloned into expression vector pTrcHisB (available from InVitrogen, San Diego, Calif.) that had been digested with BamHI. The resulting recombinant molecule pHis-nDiCP$_{945}$ was transformed into E. coli to form recombinant cell E. coli:pHis-nDiCP$_{945}$.

Example 3

This Example describes the production in bacteria of a filariid nematode cysteine protease protein of the present invention. This Example also discloses an antibody preparation produced in response to the parasitic helminth protein. Recombinant cell E. coli:pHis-nDiCP$_{945}$, produced as described in Example 2, was cultured in shake flasks containing an enriched bacterial growth medium containing 0.1 mg/ml ampicillin and 0.1% glucose at about 32° C. When the cells reached an OD$_{600}$ of about 0.4, expression of D. immitis nDiCP$_{945}$ was induced by addition of about 0.5 mM isopropyl-B-D-thiogalactoside (IPTG), and the cells cultured for about 3 hours at about 32° C. Protein production was monitored by SDS PAGE of recombinant cell lysates, followed by Coomassie blue staining, using standard techniques. Recombinant cell E. coli:pHis-nDiCP$_{945}$ produced a fusion protein, denoted herein as PHIS-PDiCP$_{314}$, that migrated with an apparent molecular weight of about 37 kD.

Immunoblot analysis of recombinant cell E. coli:pHis-nDiCP$_{945}$ lysates indicated that the about 37 kD protein was able to bind to a T7 tag monoclonal antibody (available from Novagen, Inc., Madison, Wis.) directed against the fusion portion of the recombinant PHIS-PDiCP$_{314}$ fusion protein.

The PHIS-PDiCP$_{314}$ histidine fusion peptide was separated from E. coli proteins by nickel chelation chromatography and an imidazole gradient. Immunoblot analysis of the total E. coli:pHis-nDiCP$_{945}$ lysate, column eluate and column void volume indicated that the PHIS-PDiCP$_{314}$ 37 kD protein could be isolated on the nickel column and was able to selectively bind to a T7 tag monoclonal antibody.

A rabbit was immunized twice with PHIS-PDiCP$_{314}$ that was purified by chelation chromatography. Antisera collected from this rabbit was denoted anti-PHIS-PDiCP$_{314}$ antisera.

Example 4

This Example describes the production of a D. immitis cysteine protease protein of the present invention in a eukaryotic cell.

Recombinant molecule pVL1393-nCP$_{945}$, containing a D. immitis CP nucleic acid molecule operatively linked to baculovirus polyhedron transcription control sequences was produced in the following manner. An about 945 nucleotide DNA fragment containing nucleotides spanning from about nucleotide 253 through about nucleotide 1197 of SEQ ID NO:1, called nDiCP$_{945}$, was PCR amplified from recombinant molecule pβgal-nDiCP$_{1298}$, described in Example 1, using the following primers: a sense primer BvCP sen (5' CGCGGATCCTATAAATATGAAAAAATTAGAAACC 3' (SEQ ID NO:10) and an antisense primer BvCP ant 5° CGCGGATCCTTATATGGGGAATGAAGC 3' (SEQ ID NO:11), which have BamHI sites (in bold) incorporated into the primers. The N-terminal primer was designed from the nucleic acid sequence of nDiCP$_{1298}$ with modifications to enhance expression in the baculovirus system.

The PCR product was digested with BamHI restriction endonuclease, gel purified and directionally subcloned into baculovirus shuttle plasmid pVL1393 (available from Invitrogen Inc., San Diego, Calif.) that had been cleaved with BamHI. The resulting recombinant molecule, denoted herein as pVL1393-nDiCP$_{945}$ was co-transfected into S. frugiperda Sf9 cells (donated by the Colorado Bioprocessing Center, Fort Collins, Col.) with linear wild type baculovirus DNA (ACMNPV) and insectin cationic liposomes (available from Invitrogen) to form: S. frugiperda:pVL1393-nDiCP$_{945}$.

The resulting recombinant virus, denoted vBV-nDiCP$_{945}$, was cultivated for increased production of recombinant virus and expression of PDiCP$_{314}$ was verified by Western blot. Immunoblot analysis using rabbit anti-PHIS-PDiCP$_{314}$ antisera produced as described in Example 3 demonstrated that total lysates of insect cells transfected with recombinant baculovirus vBV-nDiCP$_{945}$ expressed a protein encoded by nDiCP$_{945}$ (i.e., PDiCP$_{314}$) that migrated with an apparent molecular weight of about 35 kD.

Example 5

This Example demonstrates the use of a D. immitis CP nucleic acid molecule of the present invention to obtain a nucleic acid molecule of another filariid nematode.

O. volvulus CP nucleic acid molecule nOvCP$_{291}$ was obtained in the following manner. D. immitis nucleic acid molecule nDiCP$_{1298}$ was cleaved with EcoRI and XhoI to produce two fragments of about 850 bp and 450 bp that were gel purified and mixed hexamer labeled with Amersham's Megaprime DNA Labeling System (available from Amersham Corp., Arlington Heights, Ill.). These labeled fragments (i.e., nDiCP$_{850}$ and nDiCP$_{450}$) were used to screen an O. volvulus L3 cDNA library for plaques having nucleic acid molecules that could form stable hybrids with the D. immitis nucleic acid molecules under stringent hybridization conditions. Approximately 70,000 plaques from an O. volvulus L3 cDNA library were screened with the mixed hexamer labeled D. immitis heterologous probe using standard hybridization techniques as described by Sambrook et al., ibid. Numerous positive signals were identified from this primary hybridization screen. These regions were plugged, and the phage pools were screened further by plaque hybridization screening using the same mixed hexamer labeled D. immitis nDiCP$_{1298}$ fragment probe. One L3 cDNA clone was plaque purified, excised, and subcloned into pBluescript (available from Stratagene). Plasmid DNA was analyzed by EcoRI restriction digestion and found to contain an insert of about 290 nucleotides.

The insert of the plasmid was sequenced as described in Example 1 and determined to have about a 291-nucleotide nucleic acid sequence, represented herein as SEQ ID NO:5. A nucleic acid molecule consisting of SEQ ID NO:5 is referred to herein as nOvCP$_{291}$. Translation of SEQ ID NO:5 indicated that nOvCP$_{291}$ includes an open reading frame spanning from about nucleotide 2 through about nucleotide 217 with a stop codon nucleotides spanning from about nucleotide 218 through about nucleotide 220, followed by a 3' untranslated region spanning from about nucleotide 221 through about nucleotide 291. The open reading frame encodes a protein of about 72 amino acids, referred to herein as POvCP$_{72}$, the amino acid sequence of which is represented herein as SEQ ID NO:6. Nucleic acid molecule nOvCP$_{216}$ consists of the coding region of POvCP$_{72}$, the nucleic acid sequence of which is represented herein as SEQ ID NO:7.

Comparison of the *O. volvulus* POVCP$_{72}$ amino acid sequence with the corresponding amino acid sequence of *D. immitis* PDiCP$_{398}$ indicate that the two sequences share about 67% identity. About 77% identity was found between the amino sequence encoded by approximately 284 nucleotides of the coding region plus the proposed 3' untranslated region of the *O. volvulus* novCP$_{291}$ and the amino acid sequence of the 3' end of *D. immitis* nDiCP$_{1298}$. Comparison of the amino acid sequence of the coding region of *O. volvulus* nOvCP$_{216}$ and the corresponding region of *D. immitis* nDiCPI$_{298}$ indicate that the two sequences share about 80% identity.

About 65% identity was found between about 66 amino acids of *O. volvulus* POvCP$_{72}$ and the amino acid sequence of the 3' end of cathepsin L-like proteinase from liver fluke, *Fasciola hepatica*. About 65% identity was found between about 62 amino acids of *O. volvulus* POVCP$_{72}$ and the amino acid sequence of the 3' end of cathepsin L proteinase from parasitic trematode, *Schistosoma mansoni*. About 63% identity was found between approximately 65 amino acids of *O. volvulus* POVCP$_{72}$ and the amino acid sequence of the 3' end of chick cathepsin L (EC 3.4.22.15).

Taken together, these examples clearly indicate that knowledge of the nucleic acid sequence of *D. immitis* and *O. volvulus* cysteine protease nucleic acid molecules of the present invention enables the identification and isolation of additional filariid nematode nucleic acid molecules of the present invention.

What is claimed is:

1. An isolated protein selected from the group consisting of a *Dirofilaria immitis* L3 larval protease protein, wherein said protein is as expressed by recombinant cell ATCC 98471, and an *Onchocerca volvulus* L3 larval cysteine protease protein comprising SEQ ID NO:6.

2. The isolated protein of claim 1, wherein said protein comprises amino acid sequence SEQ ID NO:6.

3. The isolated protein of claim 1, wherein said protein is produced by a process comprising culturing a recombinant cell transformed with a nucleic acid molecule encoding said protein to produce said protein.

4. The isolated protein of claim 3, wherein said nucleic acid molecule comprises SEQ ID NO:7.

5. The protein of claim 1, wherein said protein is encoded by a *Dirofilaria immitis* nucleic acid molecule identical to that present in recombinant cell ATCC 98471.

\* \* \* \* \*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 1304 nucleotides
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1200

( x i ) SEQUENCE DESCRIPTION: SEQ ID NO:1:

```
CTT  CGA  TTC  ATT  GCT  TTA  TTG  GCC  ATA  CTC  ACT  TTC  TTG  ATC        42
Leu  Arg  Phe  Ile  Ala  Leu  Leu  Ala  Ile  Leu  Thr  Phe  Leu  Ile
 1              5                        10

GAC  TTT  ACC  GTC  TCA  TTC  AAT  GAT  GAA  ATT  CTA  CAG  CTG  AAA        84
Asp  Phe  Thr  Val  Ser  Phe  Asn  Asp  Glu  Ile  Leu  Gln  Leu  Lys
15                       20                       25

GAA  GTA  TTG  GGA  ATG  TTT  GAT  GAA  GAT  TAC  AGA  TTA  GGA  AAT       126
Glu  Val  Leu  Gly  Met  Phe  Asp  Glu  Asp  Tyr  Arg  Leu  Gly  Asn
        30                       35                       40

ATG  ACG  AGA  CTT  ACG  TTT  GAT  TTT  CAA  AAC  GCT  TTG  AAA  GAT       168
Met  Thr  Arg  Leu  Thr  Phe  Asp  Phe  Gln  Asn  Ala  Leu  Lys  Asp
             45                       50                       55

TAC  GGC  GAT  GGA  GAA  AAC  AGT  TAT  AAA  CTA  ACT  GCT  GTG  CAA       210
Tyr  Gly  Asp  Gly  Glu  Asn  Ser  Tyr  Lys  Leu  Thr  Ala  Val  Gln
                  60                       65                       70

TCT  TTC  CTC  AAA  AAA  TTA  GAA  GAA  AAC  GGT  GAG  GAA  CAA  GCG       252
Ser  Phe  Leu  Lys  Lys  Leu  Glu  Glu  Asn  Gly  Glu  Glu  Gln  Ala
                       75                       80

ATG  AAA  AAA  TTA  GAA  ACC  GAA  TGG  CAA  GAG  TAT  TTA  ACA  GCT       294
Met  Lys  Lys  Leu  Glu  Thr  Glu  Trp  Gln  Glu  Tyr  Leu  Thr  Ala
85                       90                       95

CTT  GGA  AAA  GAA  TAT  GAT  TCA  GAA  GAG  AAT  AAA  TTG  AGA  ATG       336
Leu  Gly  Lys  Glu  Tyr  Asp  Ser  Glu  Glu  Asn  Lys  Leu  Arg  Met
       100                      105                      110
```

```
GCA ATA TTT GAA AGT AAT GAA TTA ATG ACA GAA GCA TTA AAT                    378
Ala Ile Phe Glu Ser Asn Glu Leu Met Thr Glu Ala Leu Asn
    115                 120                 125

AGA AAA TAT GAG CAA GGC TTA ATT TCA TTT AAA ACT GCC CTG                    420
Arg Lys Tyr Glu Gln Gly Leu Ile Ser Phe Lys Thr Ala Leu
            130                 135                 140

AAT GAT ATG GCT GAT TTG ACC GAT CAA GAA TTC AAC CTA ATG                    462
Asn Asp Met Ala Asp Leu Thr Asp Gln Glu Phe Asn Leu Met
                145                 150

AAT GGA CTT CTA CTG CAT AAT GAA ACT TCC CAT ACA AGA AGG                    504
Asn Gly Leu Leu Leu His Asn Glu Thr Ser His Thr Arg Arg
155                 160                 165

TAT GCT CGA CAA GTA TCT GGT GAA TTT CTC AAG TAC AAT AAG                    546
Tyr Ala Arg Gln Val Ser Gly Glu Phe Leu Lys Tyr Asn Lys
    170                 175                 180

AGT ACA AAG CTG CCA AAA TAT GTT GAT TGG AGA AAG AGA GGA                    588
Ser Thr Lys Leu Pro Lys Tyr Val Asp Trp Arg Lys Arg Gly
            185                 190                 195

TAT GTC ACA CCT GCC AAA GAG CAG GGC TTG TGT GGT AGT TGT                    630
Tyr Val Thr Pro Ala Lys Glu Gln Gly Leu Cys Gly Ser Cys
                200                 205                 210

TAT GCA TTC gcT GCA GCT GCA GCA TTA GAA GCT TAT AAT AAA                    672
Tyr Ala Phe Ala Ala Ala Ala Ala Leu Glu Ala Tyr Asn Lys
                215                 220

AAG ACG AAA AAC AAA CTT CTC GAT TTA TCT CCG CAA AAT ATT                    714
Lys Thr Lys Asn Lys Leu Leu Asp Leu Ser Pro Gln Asn Ile
225                 230                 235

CTA GAT TGT ACA TGG GAT CTC GGT AAT AAT GGT TGC CAT GGT                    756
Leu Asp Cys Thr Trp Asp Leu Gly Asn Asn Gly Cys His Gly
    240                 245                 250

GGT TTC ATG AAT CCG GCA TTT TAT TAT GCA AGT AAG GCA GGT                    798
Gly Phe Met Asn Pro Ala Phe Tyr Tyr Ala Ser Lys Ala Gly
            255                 260                 265

ATT GCA TCA GAA GCG AAA TAT CCG TAT GTT CAC ACT GCA AGA                    840
Ile Ala Ser Glu Ala Lys Tyr Pro Tyr Val His Thr Ala Arg
                270                 275                 280

CGT ACA TGC TAT TGG CGG AAA GAT ATA GTT GCT GCT ACT GAT                    882
Arg Thr Cys Tyr Trp Arg Lys Asp Ile Val Ala Ala Thr Asp
                285                 290

AAT GGT TAC ACT CGA ATA CAA CAA GGT GAT GAG AAA GGT CTt                    924
Asn Gly Tyr Thr Arg Ile Gln Gln Gly Asp Glu Lys Gly Leu
295                 300                 305

CAA TAT GCT GTG GCt aAA TTt gGA CCc GTT GTT GTT GGA ATT                    966
Gln Tyr Ala Val Ala Lys Phe Gly Pro Val Val Val Gly Ile
    310                 315                 320

TCT GGA TAT CAA CAC GAT TTT AAA TTT TAT AAA TCC GGT GTC                   1008
Ser Gly Tyr Gln His Asp Phe Lys Phe Tyr Lys Ser Gly Val
            325                 330                 335

TAC TCT AGT GAT CAA TGT CGT GTT CCT AAT CAC GCA GTA CTG                   1050
Tyr Ser Ser Asp Gln Cys Arg Val Pro Asn His Ala Val Leu
                340                 345                 350

GTT GTT GGT TAT GGA ACC AGT AAA AAA CAC GGG gAT TAT TGG                   1092
Val Val Gly Tyr Gly Thr Ser Lys Lys His Gly Asp Tyr Trp
                355                 360

ATT ATT AAA AAT AGT TGG GGA ACT AAT TGG GgA AGA AAT GGA                   1134
Ile Ile Lys Asn Ser Trp Gly Thr Asn Trp Gly Arg Asn Gly
365                 370                 375

TAT GGT TAT ATG AAG CGA AAC GAA AGG AAT ATG TGT CAT ATC                   1176
Tyr Gly Tyr Met Lys Arg Asn Glu Arg Asn Met Cys His Ile
    380                 385                 390
```

```
GCT  ACG  ATG  GCT  TCA  TTC  CCC  ATA  TAA TTATGATTTA                    1213
Ala  Thr  Met  Ala  Ser  Phe  Pro  Ile
          395                      400

ATTTGTTTTC  GAAAAATATT  TATTTGCTA  ATTTTCAATA  TTTGATAATT                  1263

TTGGTTTAAT  AAAAAGAAAT  TGGGAAAAAA  AAAAAAAAAA  A                          1304
```

( 2 ) INFORMATION FOR SEQ ID NO:2:

( i ) SEQUENCE CHARACTERISTICS:
        ( A ) LENGTH: 400 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Leu  Arg  Phe  Ile  Ala  Leu  Leu  Ala  Ile  Leu  Thr  Phe  Leu  Ile
 1              5                        10

Asp  Phe  Thr  Val  Ser  Phe  Asn  Asp  Glu  Ile  Leu  Gln  Leu  Lys
15                        20                        25

Glu  Val  Leu  Gly  Met  Phe  Asp  Glu  Asp  Tyr  Arg  Leu  Gly  Asn
          30                        35                        40

Met  Thr  Arg  Leu  Thr  Phe  Asp  Phe  Gln  Asn  Ala  Leu  Lys  Asp
               45                        50                        55

Tyr  Gly  Asp  Gly  Glu  Asn  Ser  Tyr  Lys  Leu  Thr  Ala  Val  Gln
                    60                        65                        70

Ser  Phe  Leu  Lys  Lys  Leu  Glu  Glu  Asn  Gly  Glu  Glu  Gln  Ala
                    75                        80

Met  Lys  Lys  Leu  Glu  Thr  Glu  Trp  Gln  Glu  Tyr  Leu  Thr  Ala
85                        90                        95

Leu  Gly  Lys  Glu  Tyr  Asp  Ser  Glu  Glu  Asn  Lys  Leu  Arg  Met
          100                       105                       110

Ala  Ile  Phe  Glu  Ser  Asn  Glu  Leu  Met  Thr  Glu  Ala  Leu  Asn
               115                       120                       125

Arg  Lys  Tyr  Glu  Gln  Gly  Leu  Ile  Ser  Phe  Lys  Thr  Ala  Leu
                    130                       135                       140

Asn  Asp  Met  Ala  Asp  Leu  Thr  Asp  Gln  Glu  Phe  Asn  Leu  Met
                    145                       150

Asn  Gly  Leu  Leu  Leu  His  Asn  Glu  Thr  Ser  His  Thr  Arg  Arg
155                       160                       165

Tyr  Ala  Arg  Gln  Val  Ser  Gly  Glu  Phe  Leu  Lys  Tyr  Asn  Lys
          170                       175                       180

Ser  Thr  Lys  Leu  Pro  Lys  Tyr  Val  Asp  Trp  Arg  Lys  Arg  Gly
               185                       190                       195

Tyr  Val  Thr  Pro  Ala  Lys  Glu  Gln  Gly  Leu  Cys  Gly  Ser  Cys
                    200                       205                       210

Tyr  Ala  Phe  Ala  Ala  Ala  Ala  Ala  Leu  Glu  Ala  Tyr  Asn  Lys
                    215                       220

Lys  Thr  Lys  Asn  Lys  Leu  Leu  Asp  Leu  Ser  Pro  Gln  Asn  Ile
225                       230                       235

Leu  Asp  Cys  Thr  Trp  Asp  Leu  Gly  Asn  Asn  Gly  Cys  His  Gly
          240                       245                       250

Gly  Phe  Met  Asn  Pro  Ala  Phe  Tyr  Tyr  Ala  Ser  Lys  Ala  Gly
               255                       260                       265

Ile  Ala  Ser  Glu  Ala  Lys  Tyr  Pro  Tyr  Val  His  Thr  Ala  Arg
                    270                       275                       280
```

| | | | | | | | | | | | | |
|---|---|---|---|---|---|---|---|---|---|---|---|---|
| Arg | Thr | Cys | Tyr | Trp<br>285 | Arg | Lys | Asp | Ile | Val<br>290 | Ala | Ala | Thr | Asp |
| Asn<br>295 | Gly | Tyr | Thr | Arg | Ile<br>300 | Gln | Gln | Gly | Asp | Glu<br>305 | Lys | Gly | Leu |
| Gln | Tyr<br>310 | Ala | Val | Ala | Lys | Phe<br>315 | Gly | Pro | Val | Val | Val<br>320 | Gly | Ile |
| Ser | Gly | Tyr<br>325 | Gln | His | Asp | Phe | Lys<br>330 | Phe | Tyr | Lys | Ser | Gly<br>335 | Val |
| Tyr | Ser | Ser | Asp<br>340 | Gln | Cys | Arg | Val | Pro<br>345 | Asn | His | Ala | Val | Leu<br>350 |
| Val | Val | Gly | Tyr | Gly<br>355 | Thr | Ser | Lys | Lys | His<br>360 | Gly | Asp | Tyr | Trp |
| Ile<br>365 | Ile | Lys | Asn | Ser | Trp<br>370 | Gly | Thr | Asn | Trp | Gly<br>375 | Arg | Asn | Gly |
| Tyr | Gly<br>380 | Tyr | Met | Lys | Arg | Asn<br>385 | Glu | Arg | Asn | Met | Cys<br>390 | His | Ile |
| Ala | Thr | Met<br>395 | Ala | Ser | Phe | Pro | Ile<br>400 | | | | | | |

( 2 ) INFORMATION FOR SEQ ID NO:3:

( i ) SEQUENCE CHARACTERISTICS:
        ( A ) LENGTH: 950 nucleotides
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..948

( x i ) SEQUENCE DESCRIPTION: SEQ ID NO:3:

| | | | | | | | | | | | | | |
|---|---|---|---|---|---|---|---|---|---|---|---|---|---|
| ATG<br>Met<br>1 | AAA<br>Lys | AAA<br>Lys | TTA<br>Leu | GAA<br>Glu<br>5 | ACC<br>Thr | GAA<br>Glu | TGG<br>Trp | CAA<br>Gln | GAG<br>Glu<br>10 | TAT<br>Tyr | TTA<br>Leu | ACA<br>Thr | GCT<br>Ala | 42 |
| CTT<br>Leu<br>15 | GGA<br>Gly | AAA<br>Lys | GAA<br>Glu | TAT<br>Tyr | GAT<br>Asp<br>20 | TCA<br>Ser | GAA<br>Glu | GAG<br>Glu | AAT<br>Asn | AAA<br>Lys<br>25 | TTG<br>Leu | AGA<br>Arg | ATG<br>Met | 84 |
| GCA<br>Ala | ATA<br>Ile<br>30 | TTT<br>Phe | GAA<br>Glu | AGT<br>Ser | AAT<br>Asn | GAA<br>Glu<br>35 | TTA<br>Leu | ATG<br>Met | ACA<br>Thr | GAA<br>Glu | GCA<br>Ala<br>40 | TTA<br>Leu | AAT<br>Asn | 126 |
| AGA<br>Arg | AAA<br>Lys | TAT<br>Tyr<br>45 | GAG<br>Glu | CAA<br>Gln | GGC<br>Gly | TTA<br>Leu | ATT<br>Ile<br>50 | TCA<br>Ser | TTT<br>Phe | AAA<br>Lys | ACT<br>Thr | GCC<br>Ala<br>55 | CTG<br>Leu | 168 |
| AAT<br>Asn | GAT<br>Asp | ATG<br>Met | GCT<br>Ala<br>60 | GAT<br>Asp | TTG<br>Leu | ACC<br>Thr | GAT<br>Asp | CAA<br>Gln<br>65 | GAA<br>Glu | TTC<br>Phe | AAC<br>Asn | CTA<br>Leu | ATG<br>Met<br>70 | 210 |
| AAT<br>Asn | GGA<br>Gly | CTT<br>Leu | CTA<br>Leu | CTG<br>Leu<br>75 | CAT<br>His | AAT<br>Asn | GAA<br>Glu | ACT<br>Thr | TCC<br>Ser<br>80 | CAT<br>His | ACA<br>Thr | AGA<br>Arg | AGG<br>Arg | 252 |
| TAT<br>Tyr<br>85 | GCT<br>Ala | CGA<br>Arg | CAA<br>Gln | GTA<br>Val | TCT<br>Ser<br>90 | GGT<br>Gly | GAA<br>Glu | TTT<br>Phe | CTC<br>Leu | AAG<br>Lys<br>95 | TAC<br>Tyr | AAT<br>Asn | AAG<br>Lys | 294 |
| AGT<br>Ser | ACA<br>Thr<br>100 | AAG<br>Lys | CTG<br>Leu | CCA<br>Pro | AAA<br>Lys | TAT<br>Tyr<br>105 | GTT<br>Val | GAT<br>Asp | TGG<br>Trp | AGA<br>Arg | AAG<br>Lys<br>110 | AGA<br>Arg | GGA<br>Gly | 336 |
| TAT<br>Tyr | GTC<br>Val | ACA<br>Thr<br>115 | CCT<br>Pro | GCC<br>Ala | AAA<br>Lys | GAG<br>Glu | CAG<br>Gln<br>120 | GGC<br>Gly | TTG<br>Leu | TGT<br>Cys | GGT<br>Gly | AGT<br>Ser<br>125 | TGT<br>Cys | 378 |

```
TAT GCA TTC gcT GCA GCT GCA GCA TTA GAA GCT TAT AAT AAA              420
Tyr Ala Phe Ala Ala Ala Ala Ala Leu Glu Ala Tyr Asn Lys
            130                 135                 140

AAG ACG AAA AAC AAA CTT CTC GAT TTA TCT CCG CAA AAT ATT              462
Lys Thr Lys Asn Lys Leu Leu Asp Leu Ser Pro Gln Asn Ile
            145                 150

CTA GAT TGT ACA TGG GAT CTC GGT AAT AAT GGT TGC CAT GGT              504
Leu Asp Cys Thr Trp Asp Leu Gly Asn Asn Gly Cys His Gly
155                 160                 165

GGT TTC ATG AAT CCG GCA TTT TAT TAT GCA AGT AAG GCA GGT              546
Gly Phe Met Asn Pro Ala Phe Tyr Tyr Ala Ser Lys Ala Gly
        170                 175                 180

ATT GCA TCA GAA GCG AAA TAT CCG TAT GTT CAC ACT GCA AGA              588
Ile Ala Ser Glu Ala Lys Tyr Pro Tyr Val His Thr Ala Arg
            185                 190                 195

CGT ACA TGC TAT TGG CGG AAA GAT ATA GTT GCT GCT ACT GAT              630
Arg Thr Cys Tyr Trp Arg Lys Asp Ile Val Ala Ala Thr Asp
                200                 205                 210

AAT GGT TAC ACT CGA ATA CAA CAA GGT GAT GAG AAA GGT CTt              672
Asn Gly Tyr Thr Arg Ile Gln Gln Gly Asp Glu Lys Gly Leu
                    215                 220

CAA TAT GCT GTG GCt aAA TTt gGA CCc GTT GTT GTT GGA ATT              714
Gln Tyr Ala Val Ala Lys Phe Gly Pro Val Val Val Gly Ile
225                 230                 235

TCT GGA TAT CAA CAC GAT TTT AAA TTT TAT AAA TCC GGT GTC              756
Ser Gly Tyr Gln His Asp Phe Lys Phe Tyr Lys Ser Gly Val
    240                 245                 250

TAC TCT AGT GAT CAA TGT CGT GTT CCT AAT CAC GCA GTA CTG              798
Tyr Ser Ser Asp Gln Cys Arg Val Pro Asn His Ala Val Leu
        255                 260                 265

GTT GTT GGT TAT GGA ACC AGT AAA AAA CAC GGG gAT TAT TGG              840
Val Val Gly Tyr Gly Thr Ser Lys Lys His Gly Asp Tyr Trp
            270                 275                 280

ATT ATT AAA AAT AGT TGG GGA ACT AAT TGG GgA AGA AAT GGA              882
Ile Ile Lys Asn Ser Trp Gly Thr Asn Trp Gly Arg Asn Gly
                285                 290

TAT GGT TAT ATG AAG CGA AAC GAA AGG AAT ATG TGT CAT ATC              924
Tyr Gly Tyr Met Lys Arg Asn Glu Arg Asn Met Cys His Ile
295                 300                 305

GCT ACG ATG GCT TCA TTC CCC ATA TA                                   950
Ala Thr Met Ala Ser Phe Pro Ile
    310                 315
```

( 2 ) INFORMATION FOR SEQ ID NO:4:

( i ) SEQUENCE CHARACTERISTICS:
        ( A ) LENGTH: 316 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Lys Lys Leu Glu Thr Glu Trp Gln Glu Tyr Leu Thr Ala
1               5                   10

Leu Gly Lys Glu Tyr Asp Ser Glu Glu Asn Lys Leu Arg Met
    15              20                  25

Ala Ile Phe Glu Ser Asn Glu Leu Met Thr Glu Ala Leu Asn
        30                  35                  40

Arg Lys Tyr Glu Gln Gly Leu Ile Ser Phe Lys Thr Ala Leu
            45                  50                  55
```

```
Asn  Asp  Met  Ala  Asp  Leu  Thr  Asp  Gln  Glu  Phe  Asn  Leu  Met
               60                  65                            70

Asn  Gly  Leu  Leu  Leu  His  Asn  Glu  Thr  Ser  His  Thr  Arg  Arg
                    75                       80

Tyr  Ala  Arg  Gln  Val  Ser  Gly  Glu  Phe  Leu  Lys  Tyr  Asn  Lys
 85                           90                  95

Ser  Thr  Lys  Leu  Pro  Lys  Tyr  Val  Asp  Trp  Arg  Lys  Arg  Gly
     100                      105                      110

Tyr  Val  Thr  Pro  Ala  Lys  Glu  Gln  Gly  Leu  Cys  Gly  Ser  Cys
          115                      120                      125

Tyr  Ala  Phe  Ala  Ala  Ala  Ala  Leu  Glu  Ala  Tyr  Asn  Lys
               130                 135                      140

Lys  Thr  Lys  Asn  Lys  Leu  Leu  Asp  Leu  Ser  Pro  Gln  Asn  Ile
                    145                      150

Leu  Asp  Cys  Thr  Trp  Asp  Leu  Gly  Asn  Asn  Gly  Cys  His  Gly
155                      160                      165

Gly  Phe  Met  Asn  Pro  Ala  Phe  Tyr  Ala  Ser  Lys  Ala  Gly
     170                      175                 180

Ile  Ala  Ser  Glu  Ala  Lys  Tyr  Pro  Tyr  Val  His  Thr  Ala  Arg
               185                 190                      195

Arg  Thr  Cys  Tyr  Trp  Arg  Lys  Asp  Ile  Val  Ala  Ala  Thr  Asp
               200                      205                      210

Asn  Gly  Tyr  Thr  Arg  Ile  Gln  Gln  Gly  Asp  Glu  Lys  Gly  Leu
                    215                      220

Gln  Tyr  Ala  Val  Ala  Lys  Phe  Gly  Pro  Val  Val  Val  Gly  Ile
225                      230                      235

Ser  Gly  Tyr  Gln  His  Asp  Phe  Lys  Phe  Tyr  Lys  Ser  Gly  Val
     240                      245                      250

Tyr  Ser  Ser  Asp  Gln  Cys  Arg  Val  Pro  Asn  His  Ala  Val  Leu
          255                      260                      265

Val  Val  Gly  Tyr  Gly  Thr  Ser  Lys  Lys  His  Gly  Asp  Tyr  Trp
               270                      275                      280

Ile  Ile  Lys  Asn  Ser  Trp  Gly  Thr  Asn  Trp  Gly  Arg  Asn  Gly
                    285                      290

Tyr  Gly  Tyr  Met  Lys  Arg  Asn  Glu  Arg  Asn  Met  Cys  His  Ile
295                      300                      305

Ala  Thr  Met  Ala  Ser  Phe  Pro  Ile
310                      315
```

( 2 ) INFORMATION FOR SEQ ID NO:5:

( i ) SEQUENCE CHARACTERISTICS:
        ( A ) LENGTH: 291 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 2..219

( x i ) SEQUENCE DESCRIPTION: SEQ ID NO:5:

```
T  TTT  AGA  TTC  TAT  AAA  TCC  GGT  GTT  TAT  TCT  AAT  CGT  GAC  TGT  GGT      46
   Phe  Arg  Phe  Tyr  Lys  Ser  Gly  Val  Tyr  Ser  Asn  Arg  Asp  Cys  Gly
   1              5                        10                       15

GAT  CTT  AAT  CAC  GCA  GTA  CTA  CTT  GTC  GGT  TAT  GGC  AAG  CAT  AAA  ACA     94
```

```
Asp Leu Asn His Ala Val Leu Leu Val Gly Tyr Gly Lys His Lys Thr
                20                  25                  30

TAC GGA GAA TAC TGG ATT ATT AAA AAC AGC TGG GGA ACT GAT TGG GGA       142
Tyr Gly Glu Tyr Trp Ile Ile Lys Asn Ser Trp Gly Thr Asp Trp Gly
            35                  40                  45

AGA AAA GGA TAC GCT TAT ATG GCG CGA AAT AAG GGG AAC ATG TGC CAC       190
Arg Lys Gly Tyr Ala Tyr Met Ala Arg Asn Lys Gly Asn Met Cys His
        50                  55                  60

ATC GCA ACG TTG GCT TCA ATA CCC ATA TA AAAATGATTA AATTTGATTT          239
Ile Ala Thr Leu Ala Ser Ile Pro Ile
    65                  70

TGAATAGTAT TTATTGGCCA AATTCTAACT TTCATCTATG TTTGAGGGCA AT             291
```

( 2 ) INFORMATION FOR SEQ ID NO:6:

( i ) SEQUENCE CHARACTERISTICS:
        ( A ) LENGTH: 72 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Phe Arg Phe Tyr Lys Ser Gly Val Tyr Ser Asn Arg Asp Cys Gly Asp
 1               5                  10                  15

Leu Asn His Ala Val Leu Leu Val Gly Tyr Gly Lys His Lys Thr Tyr
                20                  25                  30

Gly Glu Tyr Trp Ile Ile Lys Asn Ser Trp Gly Thr Asp Trp Gly Arg
            35                  40                  45

Lys Gly Tyr Ala Tyr Met Ala Arg Asn Lys Gly Asn Met Cys His Ile
        50                  55                  60

Ala Thr Leu Ala Ser Ile Pro Ile
 65                  70
```

( 2 ) INFORMATION FOR SEQ ID NO:7:

( i ) SEQUENCE CHARACTERISTICS:
        ( A ) LENGTH: 216 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

```
TTTAGATTCT ATAAATCCGG TGTTTATTCT AATCGTGACT GTGGTGATCT TAATCACGCA      60
GTACTACTTG TCGGTTATGG CAAGCATAAA ACATACGGAG AATACTGGAT TATTAAAAAC     120
AGCTGGGGAA CTGATTGGGG AAGAAAAGGA TACGCTTATA TGGCGCGAAA TAAGGGGAAC     180
ATGTGCCACA TCGCAACGTT GGCTTCAATA CCCATA                               216
```

( 2 ) INFORMATION FOR SEQ ID NO:8:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
AACGGTGAGG ATCCAGCGAT GAAAAAATTA GAAAC                                 35
```

( 2 ) INFORMATION FOR SEQ ID NO:9:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

ATTAAAAGAT CTTTATATGG GGAATGAAGC CATCG        35

( 2 ) INFORMATION FOR SEQ ID NO:10:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CGCGGATCCT ATAAATATGA AAAAATTAGA AACC        34

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CGCGGATCCT TATATGGGGA ATGAAGC        27